US010386729B2

(12) United States Patent
Lee et al.

(10) Patent No.: US 10,386,729 B2
(45) Date of Patent: Aug. 20, 2019

(54) DYNAMIC REMOVAL OF CORRELATION OF HIGHLY CORRELATED PARAMETERS FOR OPTICAL METROLOGY

(71) Applicant: KLA-Tencor Corporation, Milpitas, CA (US)

(72) Inventors: Lie-Quan Lee, Fremont, CA (US); Leonid Poslavsky, Belmont, CA (US); Stilian Ivanov Pandev, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/293,221

(22) Filed: Jun. 2, 2014

(65) Prior Publication Data

US 2014/0358488 A1 Dec. 4, 2014

Related U.S. Application Data

(60) Provisional application No. 61/830,533, filed on Jun. 3, 2013.

(51) Int. Cl.
  *G03F 1/44* (2012.01)
  *G01N 21/25* (2006.01)
  *G03F 7/20* (2006.01)

(52) U.S. Cl.
  CPC ....... *G03F 7/70616* (2013.01); *G01N 21/255* (2013.01); *G03F 1/44* (2013.01);
  (Continued)

(58) Field of Classification Search
  CPC .................................................. G01N 21/255
  (Continued)

(56) References Cited

U.S. PATENT DOCUMENTS 6,278,519 B1 8/2001 Rosencwaig et al.
6,734,967 B1 5/2004 Piwonka-Corle et al.
(Continued)

FOREIGN PATENT DOCUMENTS

CN      1387131      12/2002
CN    101996266       3/2011
(Continued)

OTHER PUBLICATIONS

International Search Report and Written Opinion from PCT/US2013/030907 dated Jun. 24, 2013, 15 pgs.
(Continued)

*Primary Examiner* — Gregory J Toatley, Jr.
*Assistant Examiner* — Terence E Stifter, Jr.
(74) *Attorney, Agent, or Firm* — Hodgson Russ LLP

(57) ABSTRACT

Dynamic removal of correlation of highly-correlated parameters for optical metrology is described. An embodiment of a method includes determining a model of a structure, the model including a set of parameters; performing optical metrology measurement of the structure, including collecting spectra data on a hardware element; during the measurement of the structure, dynamically removing correlation of two or more parameters of the set of parameters, an iteration of the dynamic removal of correlation including: generating a Jacobian matrix of the set of parameters, applying a singular value decomposition of the Jacobian matrix, selecting a subset of the set of parameters, and computing a direction of the parameter search based on the subset of parameters. If the model does not converge, performing one or more additional iterations of the dynamic removal of correlation until the model converges; and if the model does converge, reporting the results of the measurement.

22 Claims, 11 Drawing Sheets

(52) U.S. Cl.
CPC ...... *G03F 7/70483* (2013.01); *G03F 7/70516* (2013.01); *G03F 7/70625* (2013.01)

(58) Field of Classification Search
USPC ..................................... 702/155, 190; 703/2
See application file for complete search history.

(56) References Cited

U.S. PATENT DOCUMENTS

| | | | |
|---|---|---|---|
| 7,031,848 | B2 | 4/2006 | Opsal et al. |
| 7,236,195 | B2 | 6/2007 | Quan |
| 7,428,060 | B2 | 9/2008 | Jin et al. |
| 7,460,237 | B1 | 12/2008 | Cramer |
| 7,478,019 | B2 | 1/2009 | Zangooie et al. |
| 7,532,331 | B2 | 5/2009 | Kiers et al. |
| 7,715,019 | B2 | 5/2010 | Kiers et al. |
| 7,761,178 | B2 | 7/2010 | Tian et al. |
| 7,831,528 | B2 | 11/2010 | Doddi et al. |
| 2002/0038196 | A1 | 3/2002 | Johnson et al. |
| 2002/0158193 | A1 | 10/2002 | Sezginer et al. |
| 2003/0028358 | A1 | 2/2003 | Niu et al. |
| 2004/0017575 | A1 | 1/2004 | Balasubramanian et al. |
| 2004/0037473 | A1 | 2/2004 | Bao et al. |
| 2004/0039473 | A1* | 2/2004 | Bao et al. .................. 700/121 |
| 2004/0070772 | A1 | 4/2004 | Shchegrov et al. |
| 2004/0090629 | A1 | 5/2004 | Drege et al. |
| 2006/0290947 | A1 | 12/2006 | Li et al. |
| 2007/0239369 | A1 | 10/2007 | Funk et al. |
| 2007/0239383 | A1 | 10/2007 | Funk et al. |
| 2008/0068616 | A1 | 3/2008 | Kiers et al. |
| 2009/0083013 | A1 | 3/2009 | Li et al. |
| 2009/0237676 | A1 | 9/2009 | Kiers et al. |
| 2010/0025807 | A1 | 2/2010 | Bowman |
| 2010/0225913 | A1 | 9/2010 | Trainer |
| 2010/0245807 | A1 | 9/2010 | Li et al. |
| 2011/0288822 | A1 | 11/2011 | Veldman et al. |
| 2011/0307424 | A1 | 12/2011 | Jin et al. |
| 2011/0307438 | A1* | 12/2011 | Fernandez Martinez ....... 706/52 |
| 2012/0022836 | A1 | 1/2012 | Ferns et al. |
| 2012/0086940 | A1 | 4/2012 | Shih et al. |
| 2012/0123581 | A1 | 5/2012 | Smilde et al. |
| 2012/0123748 | A1* | 5/2012 | Aben et al. .................. 703/2 |
| 2012/0323356 | A1 | 12/2012 | Dziura et al. |
| 2013/0110477 | A1 | 5/2013 | Pandev |
| 2013/0262044 | A1 | 10/2013 | Pandev et al. |
| 2013/0282343 | A1 | 10/2013 | Brill et al. |
| 2013/0304408 | A1 | 11/2013 | Pandev |
| 2014/0358488 | A1 | 12/2014 | Lee et al. |
| 2015/0058813 | A1 | 2/2015 | Kim et al. |

FOREIGN PATENT DOCUMENTS

| | | |
|---|---|---|
| CN | 102509001 | 6/2012 |
| CN | 102638290 | 8/2012 |
| CN | 103026204 | 4/2013 |
| JP | S62219069 | 9/1987 |
| JP | H10962647 | 3/1997 |
| WO | 2006091361 | 8/2006 |
| WO | WO 2006/091361 | 8/2006 |
| WO | WO-2006/091361 | 8/2006 |

OTHER PUBLICATIONS

David Gay, "Computing Optimal Locally Constrained Steps," SIAM J, Sci. Stat. Comput., 2:186-197, 1981.
Gavin, H., "The Levenberg-Marquardt method for nonlinear least squares curve-fitting problems," Duke University, Oct. 9, 2013, 17 pages.
Stefan Finsterle et al., "A truncated Levenberg-Marquardt algorithm for the calibration of highly parameterized nonlinear models," Computers & Geosciences, 37:731-738, 2011.
International Preliminary Report on Patentability of the International Searching Authority dated Oct. 9, 2014, in International Patent Application No. PCT/US2013/030907, 12 pages.
International Search Report and Written Opinion of the International Searching Authority dated Jun. 24, 2013, in International Patent Application No. PCT/US2013/030907, 15 pages.
Office Action dated Jun. 12, 2015, in U.S. Appl. No. 13/781,474, 19 pages.
International Search Report and Written Opinion of the International Searching Authority dated Sep. 26, 2014, in International Patent Application No. PCT/US2014/040639, 10 pages.
Final Office Action dated Jan. 21, 2016, in U.S. Appl. No. 13/781,474, 21 pages.
Levenberg, A Method for the Solution of Certain Non-Linear Problems in Least Squares, Quarterly of Applied Mathematics 2: 164-168, 1944.
Taiwan Intellectual Property Office, Office Action, Application No. 103119303 (Jan. 8, 2018).
State Intellectual Property Office, China, Office Action, Application No. 201480037324.0 (Aug. 1, 2018).

* cited by examiner

DYNAMIC REMOVAL OF CORRELATION OF HIGHLY CORRELATED PARAMETERS FOR OPTICAL METROLOGY

CROSS-REFERENCE TO RELATED APPLICATIONS

This application claims the benefit of U.S. Provisional Application No. 61/830,533, filed Jun. 3, 2013, the entire contents of which are hereby incorporated by reference herein.

TECHNICAL FIELD

Embodiments described herein generally relate to the field of metrology and, more particularly, dynamic removal of correlation of highly correlated parameters for optical metrology.

BACKGROUND

A rigorous coupled wave analysis (RCWA) and similar algorithms have been widely used for the study and design of diffraction structures. In the RCWA approach, the profiles of periodic structures are approximated by a given number of sufficiently thin planar grating slabs. Specifically, RCWA involves three main operations, namely, the Fourier expansion of the field inside the grating, calculation of the eigenvalues and eigenvectors of a constant coefficient matrix that characterizes the diffracted signal, and solution of a linear system deduced from the boundary matching conditions. RCWA divides the problem into three distinct spatial regions: (1) the ambient region supporting the incident plane wave field and a summation over all reflected diffracted orders, (2) the grating structure and underlying non-patterned layers in which the wave field is treated as a superposition of modes associated with each diffracted order, and (3) the substrate containing the transmitted wave field.

The input to the RCWA calculation is a profile or model of the periodic structure. In some cases cross-sectional electron micrographs are available (from, for example, a scanning electron microscope or a transmission electron microscope). When available, such images can be used to guide the construction of the model. However a wafer cannot be cross sectioned until all desired processing operations have been completed, which may take many days or weeks, depending on the number of subsequent processing operations. Even after all the desired processing operations are complete, the process to generate cross sectional images can take many hours to a few days because of the many operations involved in sample preparation and in finding the right location to image. Furthermore the cross section process is expensive because of the time, skilled labor and sophisticated equipment needed, and it destroys the wafer.

However, among other issues, parameters of a model of a structure may be highly correlated, thus resulting an unstable search direction during parameter measurement as the change of an objective function due to one parameter can be largely compensated by changes of its highly correlated parameter. While there are certain means of addressing correlation of parameters, the correlation of parameters may vary widely over a spectrum, and thus conventional means may not provide adequate parameterization for a model.

SUMMARY

Embodiments of the present invention include dynamic removal of correlation of highly correlated parameters for optical metrology.

In a first embodiment, a method includes determining a model of a structure, the model including a set of parameters; performing optical metrology measurement of the structure, including collecting spectra data on a hardware element; and during the measurement of the structure, dynamically removing correlation of two or more parameters of the set of parameters, an iteration of the dynamic removal of correlation including: generating a Jacobian matrix of the set of parameters, applying a singular value decomposition of the Jacobian matrix, selecting a subset of the set of parameters, and computing a direction of the parameter search based on the subset of parameters. If the model does not converge, performing one or more additional iterations of the dynamic removal of correlation until the model converges; and if the model does converge, reporting the results of the measurement.

In a second embodiment, a machine-accessible storage medium has instructions stored thereon that cause a data processing system to perform a method of dynamic removal of correlation of parameters. The method includes determining a model of a structure, the model including a set of parameters; performing optical metrology measurement of the structure, including collecting spectra data on a hardware element; and during the measurement of the structure, dynamically removing correlation of two or more parameters of the set of parameters, an iteration of the dynamic removal of correlation including: generating a Jacobian matrix of the set of parameters, applying a singular value decomposition of the Jacobian matrix, selecting a subset of the set of parameters, and computing a direction of the parameter search based on the subset of parameters. If the model does not converge, performing one or more additional iterations of the dynamic removal of correlation until the model converges; and if the model does converge, reporting the results of the measurement.

In a third embodiment, a system includes an optical metrology system configured to determine the one or more process parameters of a target structure, the optical metrology system including a beam source and detector configured to measure a diffraction signal of the structure, and a processor configured to process measurement data. The optical metrology system is configured to perform optical metrology measurement of the structure during the measurement of the structure; dynamically remove correlation of two or more parameters of the set of parameters, an iteration of the dynamic removal of correlation including: generating a Jacobian matrix of the set of parameters, applying a singular value decomposition of the Jacobian matrix, selecting a subset of the set of parameters, and computing a direction of the parameter search based on the subset of parameters; if the model does not converge, perform one or more additional iterations of the dynamic removal of correlation until the model converges; and if the model does converge, report the results of the measurement.

BRIEF DESCRIPTION OF THE DRAWINGS

Embodiments described here are illustrated by way of example, and not by way of limitation, in the figures of the accompanying drawings in which like reference numerals refer to similar elements.

DETAILED DESCRIPTION

Figure 1:
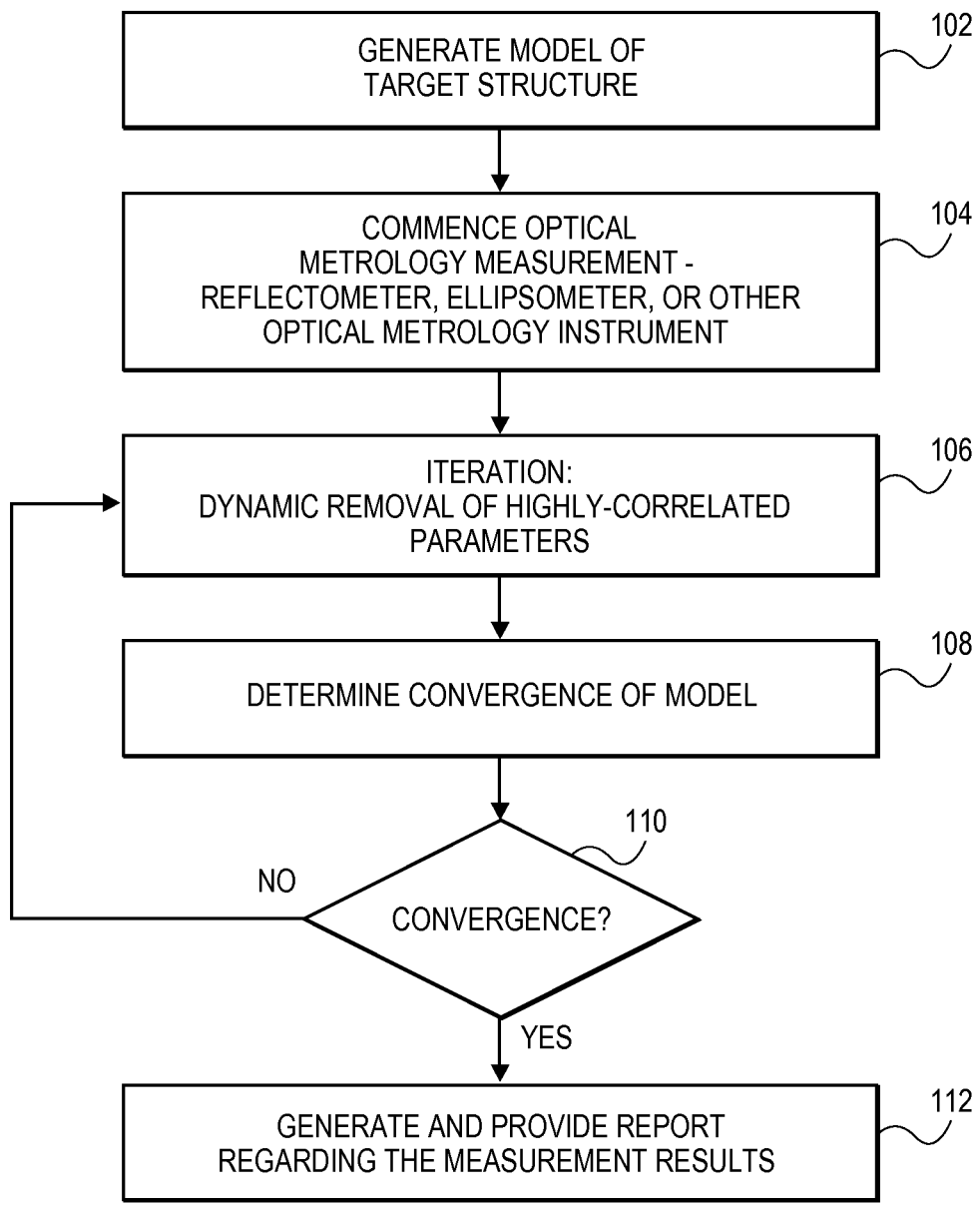
FIG. 1 is a flow chart illustrating a process for optical metrology including dynamic removal of correlation of highly-correlated parameters according to an embodiment.

Embodiments described herein are generally directed to dynamic removal of correlation of highly correlated parameters for optical metrology.

In the following description, numerous specific details are set forth, such as specific approaches to dynamic removal of correlation of parameters, in order to provide a thorough understanding of embodiments of the present invention. It will be apparent to one skilled in the art that embodiments of the present invention may be practiced without these specific details. In other instances, well-known processing operations, such as fabricating stacks of patterned material layers, are not described in detail in order to not unnecessarily obscure embodiments of the present invention. Furthermore, it is to be understood that the various embodiments shown in the figures are illustrative representations and are not necessarily drawn to scale.

One or more embodiments described herein are directed to testing and analysis based on spectral reflection and diffraction. Uses for such methods may include, for example, applications for metrology, such as optical metrology, including measurement in testing of microelectronic structures.

In some embodiments, a search method is applicable to optimization-based metrology to dynamically remove the correlation of model parameters without changing the model of a structure. In some embodiments, a method provides for dynamically removing the correlation of model parameters during the measurement process.

One or more embodiments presented herein provide new approaches to optical metrology measurement of repeating structures on a semiconductor substrate or wafer, such approaches including dynamic removal of correlation of highly-correlated parameters. For purposes of this description, "highly-correlated parameters" means parameters of a model that are correlated to any degree that may interfere with an operation. In some embodiments, the model parameters correlation may be significantly reduced dynamically, producing a model with enhanced stability.

In some embodiments, an apparatus, system, or method dynamically removes the correlation of parameters without the need to change the model of a structure. This can be very important when the correction of parameters changes drastically over the search space.

Conventionally, parametric models are defined with their geometric and material parameters. Parameter sensitivities are evaluated through simulation, and fixed error analysis may be performed to determine a suitable set of parameters to be floated. However, in many cases such parameters are highly correlated, which can render the model unstable and can introduce effects such as toggling. Fixing one or more of the correlated parameters can render the model more stable, but such fixing may introduce significant errors in the final results.

Existence of highly-correlated parameters makes search direction unstable during parameter measurement as the change of an objective function due to one parameter can be largely compensated by changes of its highly correlated parameter (or parameter set). If the parameter correlation is static, such that the correlation does not change over the parameter search space, then the processes presented in U.S. patent application Ser. No. 13/781,474, filed Feb. 28, 2013 and titled "Model Optimization Approach Based on Spectral Sensitivity," which is incorporated by reference in its entirety for all purposes, may be applied to effectively reduce the correlation through re-parameterization. However, in a circumstance in which the parameter correlation changes significantly over different parts of the search space there is additional difficulty that may reduce the usefulness of a static solution.

In some embodiments, an apparatus, process, or system operates to dynamically remove the correlation of model parameters during the measurement process so that apparatus, process, or system can successfully address a circumstance in which the correlation strongly depends on the particular location in the search space.

Processes presented in U.S. patent application Ser. No. 13/781,474 utilize re-parameterization of the geometric model with abstract parameters. In some embodiments, an apparatus, process, or system may utilize a same geometric model without requiring re-parameterization.

A nonlinear least square regression is commonly used in parameter measurement. The nonlinear least square regression minimizes the difference between the measured spectra from ellipsometers, reflectometers, or both and the calculated spectra, either from a rigorous electromagnetic solution or a fast and accurate approximation. Newton-based optimization techniques are often used in such minimization.

A Newton-based optimization is an iterative process to solve a nonlinear least square problem. Given a function: $f(x) = \sum_{i=1}^{m}(\xi_i - \bar{\xi}_i)^2 \equiv \sum_{i=1}^{m} r_i^2$, where $\bar{\xi}_i$ is a set of m measured values and $\xi_i$ a set of calculated values that depend on x, a set of n geometric or material parameters are to be determined.

In each iteration, a search direction $\Delta x$ is calculated through solving the following equation:

$$H\Delta x = -J^T R \qquad [1]$$

where H is the Hessian $\nabla^2 f$ (or an approximation in practical situations, a Hessian matrix being a square matrix of second-order partial derivatives of a function), and wherein J the Jacobian matrix (a Jacobian matrix being a matrix of first-order partial derivatives of a function) and R the residual vector are defined as follows:

$$J_{i,j} \equiv \frac{\partial r_j}{\partial x_i}\bigg|_{\substack{j=1,2,\ldots,m \\ i=1,2,\ldots,n}} \quad [2]$$

And:

$$R=(r_1,r_2,r_3,\ldots,r_m)$$

When parameters are strongly correlated, the n×n matrix H is often close to singular (indicating a matrix without an inverse, having a determinant of zero). Therefore, the solution of equation [1] may contain a large error, which takes the search direction away from the global minimum and may result in a failure to converge, or in a large number of iterations in a best case.

Other methods have been applied to address general circumstances regarding parameter search issues. In an example, $J^T J+\lambda I$ with a positive $\lambda$, may be used for H so that it is always positive definite. However, most existing methods are too general and do not tackle the root cause, the cause being the highly-correlated parameters.

The sensitivity-based re-parameterization method presented in U.S. patent application Ser. No. 13/781,474 may require an explicit change of the model parameterization. After re-parameterization of the geometric model, the floating parameters are abstract and may have no physical meaning. However, critical geometric parameters with physical meanings that are known by customers may be contained in the multiple abstract parameters, and there may be no easy way to intuitively manipulate such abstract parameters.

In some embodiments, because the matrix H is often $J^T J$ plus some augments, this may be denoted as $H=J^T J+S$. S may be zero, identity, a diagonal matrix, or other form. If S is zero, the process is reduced to a truncated-SVD regularized Gauss-Newton method.

A thin singular value decomposition (SVD) of J is calculated as:

$$J=M_n \Sigma_n V^T \quad [3]$$

with $\Sigma_n$ being a diagonal matrix and its elements sorted in non-ascending order. In some embodiments, in the special case in which the decomposition $M_n \Sigma_n V^T$ is fixed over all the search space, this value can be pre-calculated instead of being dynamically calculated.

In some embodiments, a variation of singular value decomposition or similar methods may be applied. In some embodiments, a singular value decomposition or the like can be applied to Jacobian matrix J, $J^T J$, or H matrix directly, where H matrix is an approximation of the true Hessian. In some embodiments, a method provides for linking the threshold of singular value decomposition with the noise specification.

If equation [3] is inserted into equation [1], the result is the following:

$$(\Sigma_n^2+V^T S V)V^T \Delta x=-\Sigma_n U_n^T R$$

If only the first k of the n unknowns in $V^T \Delta x$ are selected and it is denoted that $\Delta p \equiv V_k^T \Delta x$, then the following resulting equation is to be solved:

$$(\Sigma_k^2+V_k^T S V_k)\Delta p=-\Sigma_n U_k^T R \quad [4]$$

In some embodiments, a trust region treatment may be applied to equation [4]. Once $\Delta p$ is calculated, $\Delta x$ may be recovered from $\Delta x=V_{kT}\Delta p$.

Mathematically, $\Delta x$ can be added with $V_{k+1,n}q$ where q is an arbitrary vector with size of n–k, and the objective function value does not change. There may be created n–k constraints for parameter set x to remove this uncertainty. The constraints are the additional knowledge provided by, for example, application scientists. In some embodiments, an apparatus, system, or method provides for creating a set of constraints to remove uncertainty in a mathematical model of an apparatus. For example, a subset of the parameter set may be created to be similar to parameters in a predefined nominal parameter set due to process knowledge. In some embodiments, the constraints may be applied in each iteration of a calculation, or may be only applied to the last iteration. In some embodiments, the described procedure may be dynamically applied in each iteration of the Newton-based optimization. In some embodiments, the constraints may be created based upon geometric similarity to a predefined nominal geometry, direct process knowledge such as the ratio of two parameters, the difference of two parameters, the summation of all the depth parameters, or other knowledge.

In some embodiments, a search method is applicable to optimization-based metrology to dynamically remove the correlation of model parameters without changing the model.

In some embodiments, a method is to dynamically remove the correlation of model parameters during a measurement process.

In some embodiments, a method is to link the threshold of singular value decomposition with a noise specification.

In some embodiments, a method is to adaptively select the threshold in an optimization iteration.

In some embodiments, a method is to create a set of constraints to remove uncertainty in a mathematical model.

FIG. 1 is a flow chart illustrating a process for optical metrology including dynamic removal of correlation of highly correlated parameters. In some embodiments, a model is generated of a target structure 102, wherein the structure may include a structure on a semiconductor wafer. In some embodiments, optical metrology testing of the target structure is commenced, wherein the testing includes use of a spectroscopic or angle-resolved ellipsometer, spectroscopic or angle-resolved reflectometer, or other optical metrology instrument 104.

In some embodiments, the testing process includes dynamic removal of correlation of highly-correlated parameters 106, such as described above. In some embodiments, the dynamic removal of correlation includes removal of parameter correlation that varies throughout the search field.

In some embodiments, the process continues with the determination of convergence of the data 108, and, if there is convergence 110, this may be followed by the generation and provision of a report regarding the test results 112, which may be utilized in the evaluation of the test structure. If there is no convergence 110, the process may continue with one or more additional iterations of the removal of correlated parameters 106.

Figure 2:
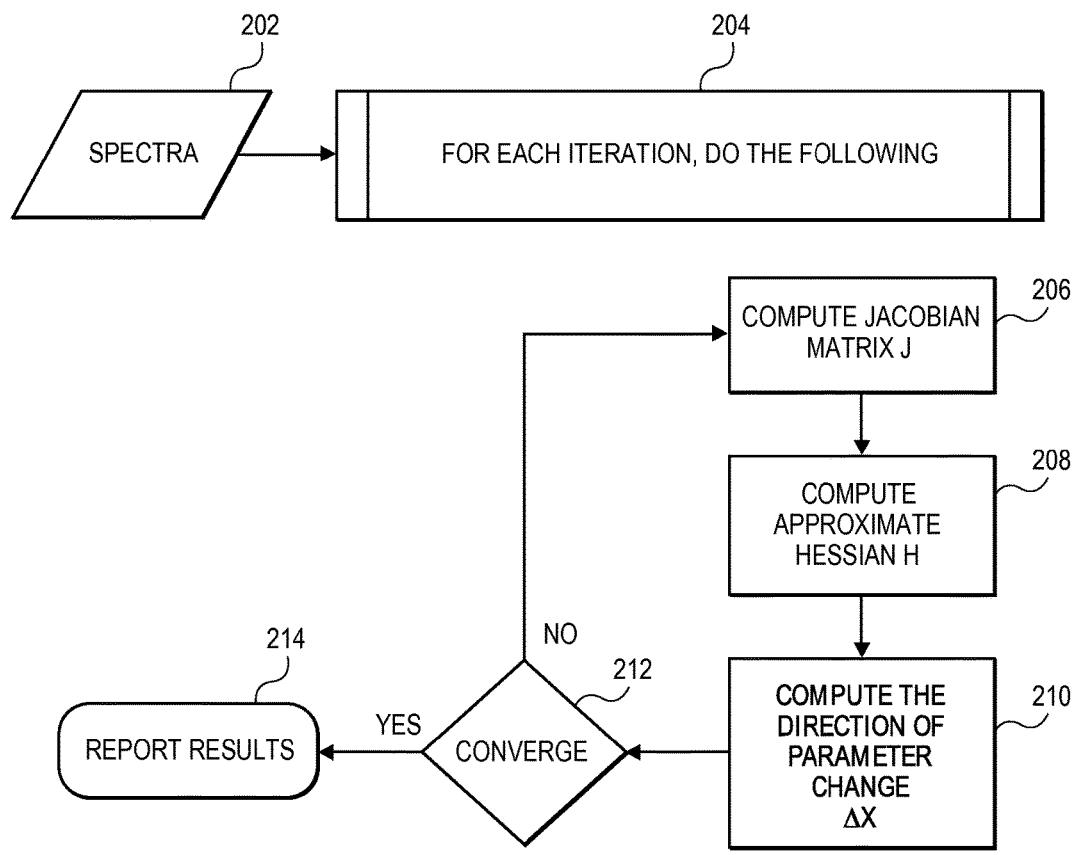
FIG. 2 is an illustration of a process of measurement without dynamic de-correlation of parameters.

FIG. 2 is an illustration of a process of measurement without dynamic de-correlation of parameters. As illustrated, in a search of a spectra space 202, for each optimization iteration 204 the process may be the following:

The Jacobian matrix J is computed 206, and an approximate Hessian H is computed 208. The direction Δx is then computed from the resulting equation 210.

If the model does not converge 212, the process returns to the calculation of the Jacobian matrix J 206. If the model does converge 212, the results then are reported 214.

Figure 3:
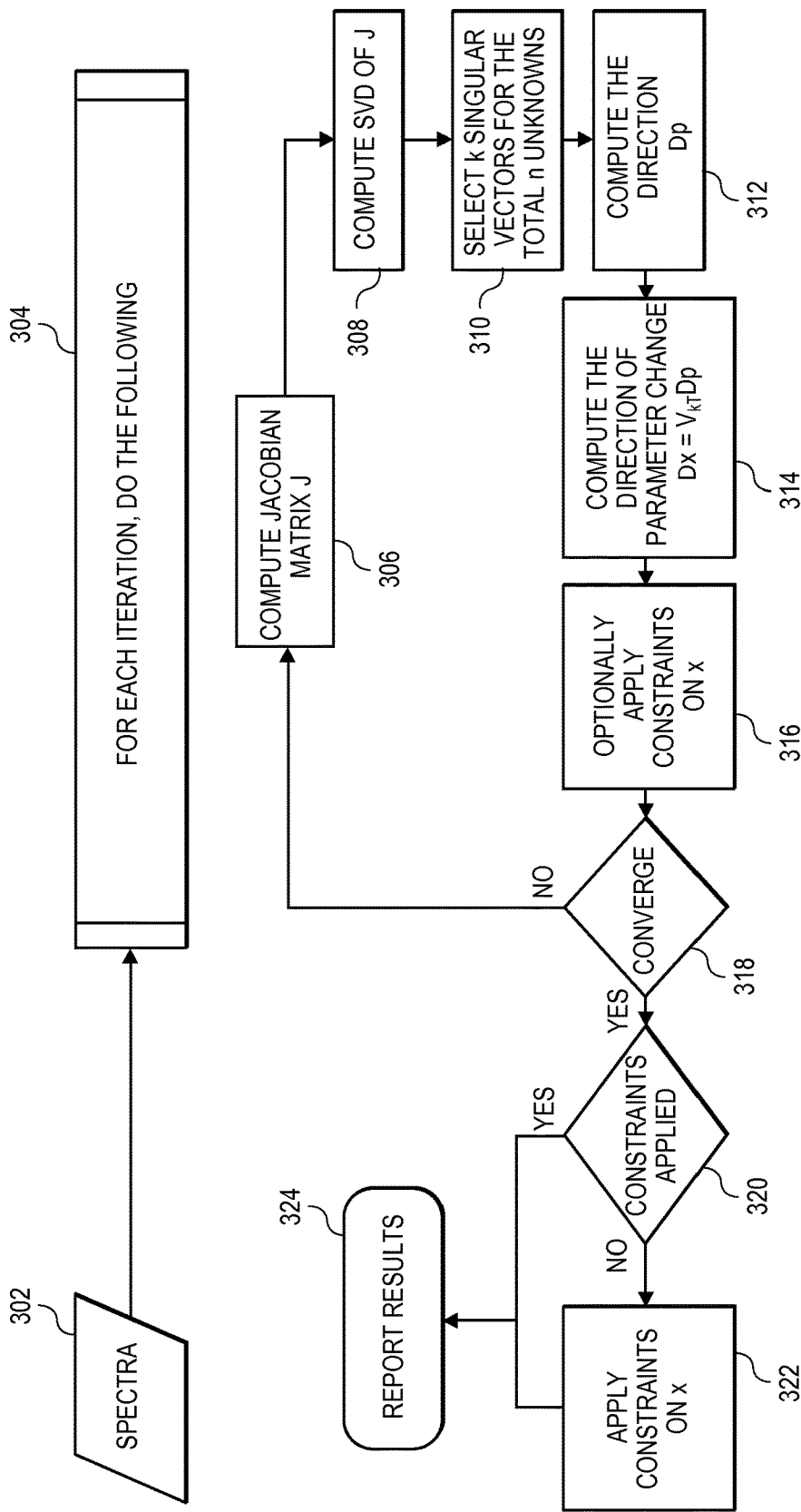
FIG. 3 is an illustration of an embodiment of a process for measurement providing dynamic de-correlation of parameters.

FIG. 3 is an illustration of an embodiment of a process for measurement providing dynamic de-correlation of parameters. As illustrated, a search of a spectra space is performed in the collection of spectra data 302. In some embodiments, for each optimization iteration 304, the following process is conducted:

In contrast with the operation illustrated in FIG. 2, the Jacobian matrix J is computed 306, and the SVD (Singular Value Decomposition) of J is computed 308. A selection of k singular vectors for the total n unknowns is made 310.

The direction Δp is then computed 312, and the direction of the parameter change $\Delta x = V_{kT} \Delta p$ is calculated 314. Optionally, constraints on x may be added at this point 316 (thus applying the constraints in each iteration), where such constraints reflect additional knowledge regarding the model.

If the model does not converge 318, the process returns to the calculation of the Jacobian matrix J 306. If the model does converge 318, then, if constraints have not yet been applied 320, constraints on x may be applied 322 (thus applying the constraints only in the final iteration). The results then are reported 324.

Details regarding the computation of the direction Δp are described above. It is noted that k, the number of items in direction Δp, can be smaller than the number of unknown parameters (x's). Physically, this indicates that the optimization is eliminating (throwing away) certain search directions that do not significantly change the objective function values when change is along one or combination of those directions.

Further, it is noted that the selection of the first k singular vectors of the total n unknowns in $V^T \Delta x$ can be challenging. In some embodiments, a first method for selection of the vectors is to use a relative ratio of the contribution of each of the singular values. For example, a relative threshold may used such that the total contribution of the first k singular vectors is >=99% of the total.

In some embodiments, a second method for selection of the vectors is to apply an absolute value. For example, selecting the first k so that all singular vectors whose singular value is larger than a certain threshold value (in an example, $10^{-6}$) are selected. The absolute threshold is related to the noise specification from a particular hardware (ellipsometers and reflectometers, etc.) on which spectra data are collected.

In some embodiments, an adaptive selection of vectors in the optimization integration may be applied. For example, at the beginning of the optimization iterations, the relative or absolute threshold may be large. The threshold may gradually change to a prescribed value as the number of iterations increases. This means that, at the beginning, the optimization adjusts parameter values that are largely sensitive and quickly reduces the objective function. Then, the optimization adaptively includes more search directions to fine tune parameter values.

In general, orders of a diffraction signal may be simulated as being derived from a periodic structure. The zeroth order represents a diffracted signal at an angle equal to the angle of incidence of a hypothetical incident beam, with respect to the normal N of the periodic structure. Higher diffraction orders are designated as +1, +2, +3, −1, −2, −3, etc. Other orders known as evanescent orders may also be considered. In accordance with an embodiment of the present invention, a simulated diffraction signal is generated for use in optical metrology. For example, profile parameters, such as structural shape and film thicknesses, may be modeled for use in optical metrology. Optical properties of materials, such as index of refraction and coefficient of extinction, (n & k), in structures may also be modeled for use in optical metrology.

Figure 4:
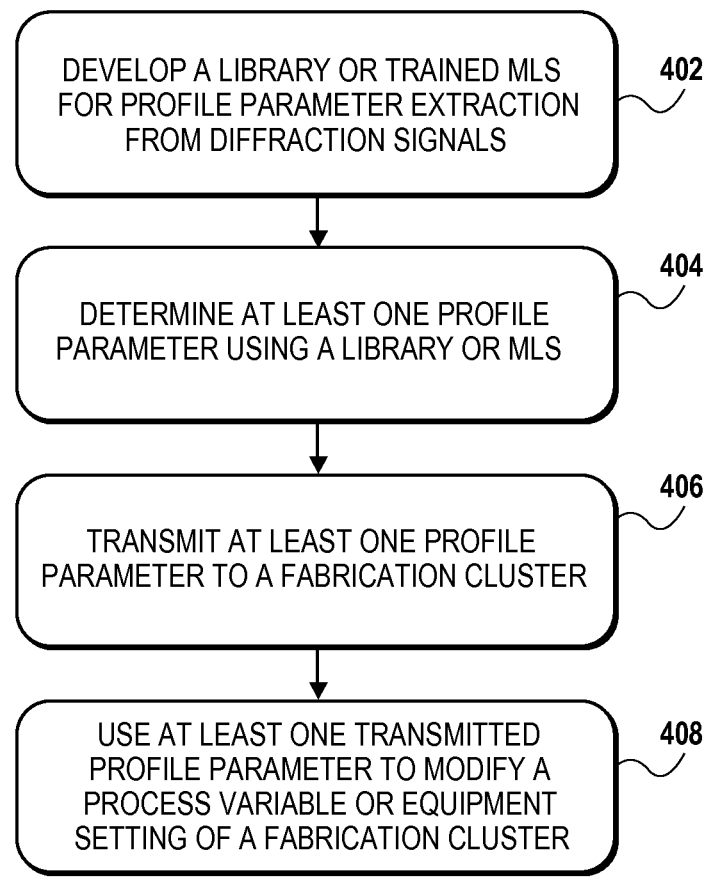
FIG. 4 depicts a flowchart representing an exemplary series of operations for determining and utilizing structural parameters for automated process and equipment control in accordance with an embodiment.

Calculations based on simulated diffraction orders may be indicative of profile parameters for a patterned film, such as a patterned semiconductor film or structure based on a stack of films, and may be used for calibrating automated processes or equipment control. FIG. 4 depicts a flowchart 400 representing an exemplary series of operations for determining and utilizing structural parameters for automated process and equipment control, in accordance with an embodiment of the present invention.

Referring to operation 402 of flowchart 400, a library or trained machine learning systems (MLS) is developed to extract parameters from a set of measured diffraction signals. In operation 404, at least one parameter of a structure is determined using the library or the trained MLS. In operation 406, the at least one parameter is transmitted to a fabrication cluster configured to perform a processing operation, where the processing operation may be executed in the semiconductor manufacturing process flow either before or after measurement operation 404 is made. In operation 408, the at least one transmitted parameter is used to modify a process variable or equipment setting for the processing operation performed by the fabrication cluster.

For a more detailed description of machine learning systems and algorithms, see U.S. Pat. No. 7,831,528, entitled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety. For a description of diffraction order optimization for two-dimensional repeating structures, see U.S. Pat. No. 7,428,060, entitled OPTIMIZATION OF DIFFRACTION ORDER SELECTION FOR TWO-DIMENSIONAL STRUCTURES, filed on Mar. 24, 2006, which is incorporated herein by reference in its entirety.

Figure 5:
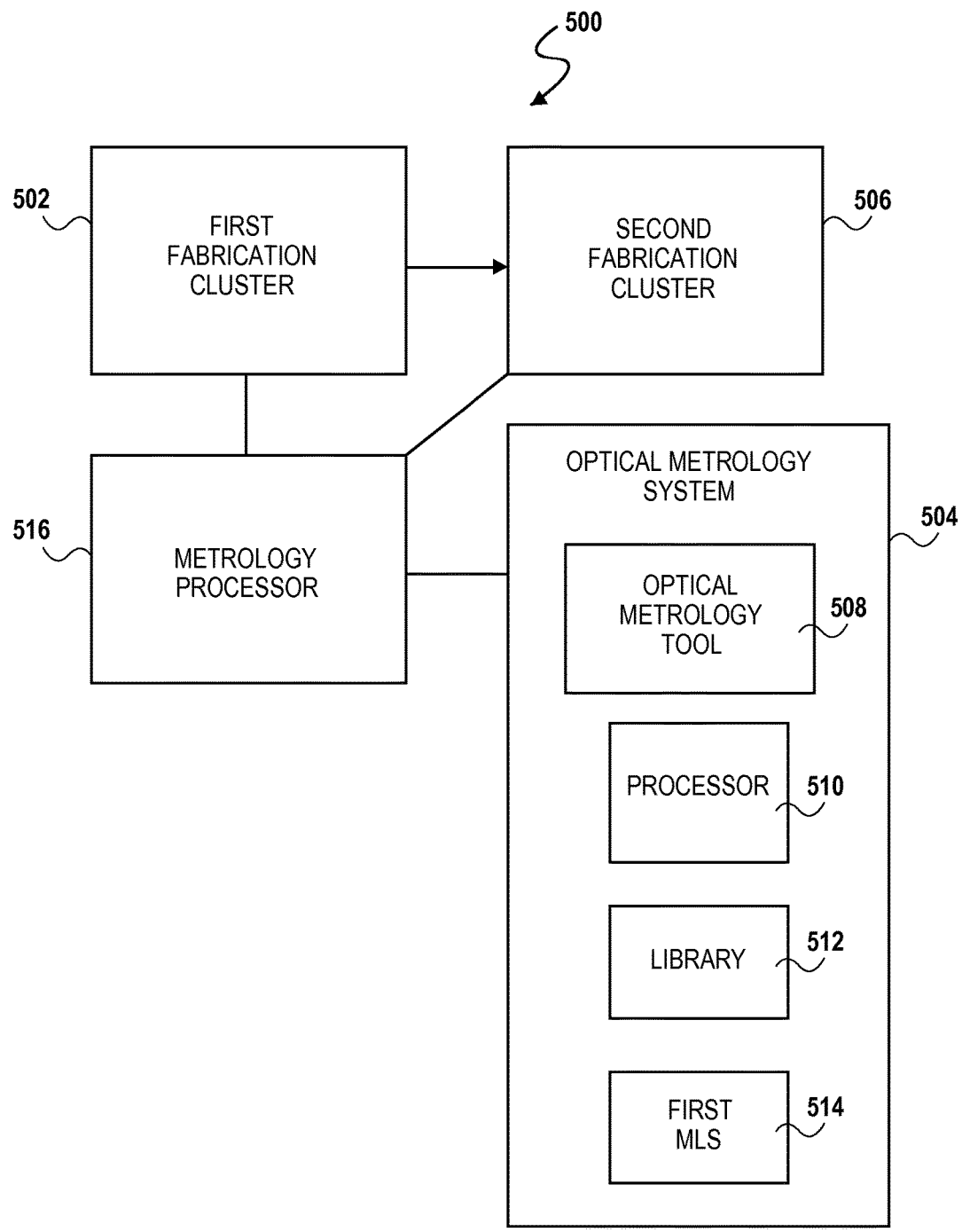
FIG. 5 is an exemplary block diagram of a system for determining and utilizing structural parameters for automated process and equipment control in accordance with an embodiment.

FIG. 5 is an exemplary block diagram of a system 500 for determining and utilizing structural parameters, such as profile or film thickness parameters, for automated process and equipment control, in accordance with an embodiment. System 500 includes a first fabrication cluster 502 and optical metrology system 504. System 500 also includes a second fabrication cluster 506. Although the second fabrication cluster 506 is depicted in FIG. 5 as being subsequent to first fabrication cluster 502, it should be recognized that second fabrication cluster 506 can be located prior to first fabrication cluster 502 in system 500 (and, e.g., in the manufacturing process flow).

In one exemplary embodiment, optical metrology system 504 includes an optical metrology tool 508 and processor 510. Optical metrology tool 508 is configured to measure a diffraction signal obtained from the structure. If the measured diffraction signal and the simulated diffraction signal match, one or more values of the profile or film thickness parameters are determined to be the one or more values of the profile or film thickness parameters associated with the simulated diffraction signal.

In one exemplary embodiment, optical metrology system 504 can also include a library 512 with a plurality of simulated diffraction signals and a plurality of values of, e.g., one or more profile or film thickness parameters associated with the plurality of simulated diffraction signals. As described above, the library can be generated in advance. Metrology processor 510 can be used to compare a measured diffraction signal obtained from a structure to the plurality of simulated diffraction signals in the library. When a matching simulated diffraction signal is found, the one or more values of the profile or film thickness parameters associated with the matching simulated diffraction signal in the library is assumed to be the one or more values of the profile or film thickness parameters used in the wafer application to fabricate the structure.

System 500 also includes a metrology processor 516. In one exemplary embodiment, processor 510 can transmit the one or more values of the, e.g., one or more profile or film thickness parameters to metrology processor 516. Metrology processor 516 can then adjust one or more process parameters or equipment settings of first fabrication cluster 502 based on the one or more values of the one or more profile or film thickness parameters determined using optical metrology system 504. Metrology processor 516 can also adjust one or more process parameters or equipment settings of the second fabrication cluster 506 based on the one or more values of the one or more profile or film thickness parameters determined using optical metrology system 504. As noted above, fabrication cluster 506 can process the wafer before or after fabrication cluster 502. In another exemplary embodiment, processor 510 is configured to train machine learning system 514 using the set of measured diffraction signals as inputs to machine learning system 514 and profile or film thickness parameters as the expected outputs of machine learning system 514.

In some embodiments, the system 500 include dynamic removal of correlation of highly-correlated parameters of a target structure, where the dynamic removal of correlation includes operations of the processor 510 in performing calculations regarding such parameters.

Figure 6A:
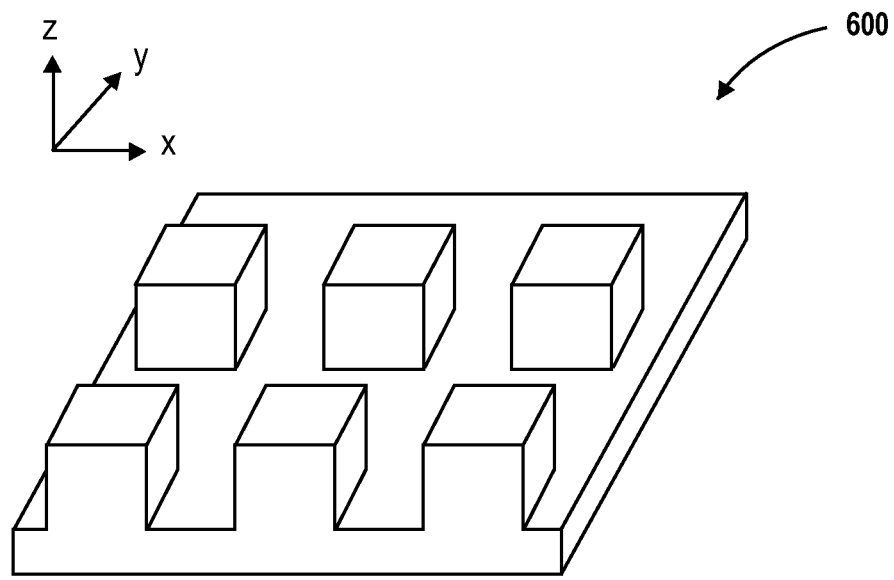
FIG. 6A depicts a periodic grating having a profile that varies in the x-y plane in accordance with an embodiment.

In some embodiments, dynamically removing correlation of parameters of a model of a structure includes a model of a three-dimensional grating structure. The term "three-dimensional grating structure" is used herein to refer to a structure having an x-y profile that varies in two horizontal dimensions in addition to a depth in the z-direction. For example, FIG. 6A depicts a periodic grating 600 having a profile that varies in the x-y plane, in accordance with an embodiment of the present invention. The profile of the periodic grating varies in the z-direction as a function of the x-y profile.

Figure 6B:
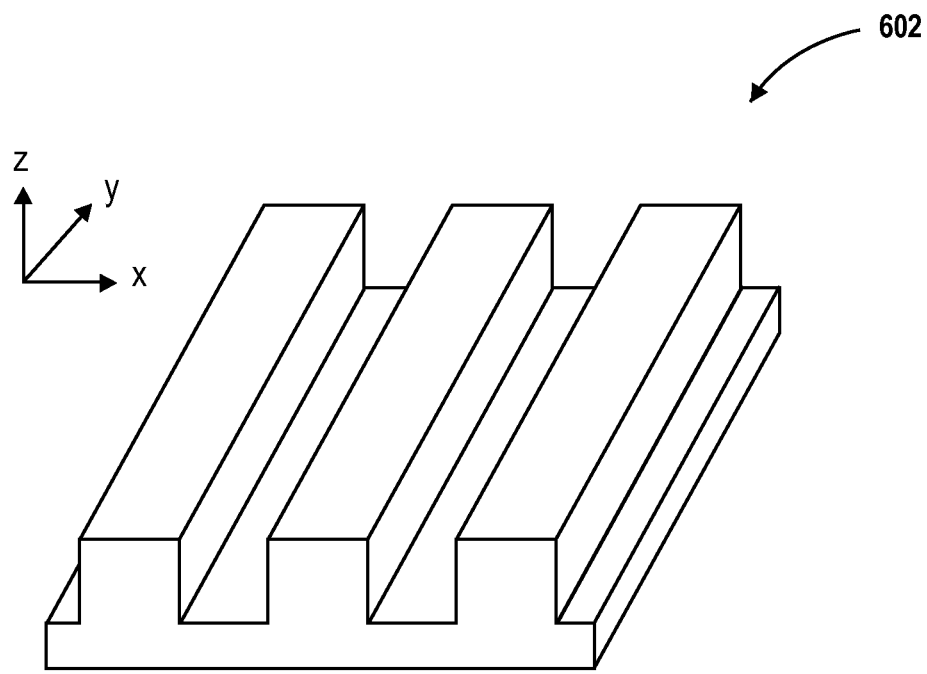
FIG. 6B depicts a periodic grating having a profile that varies in the x-direction but not in the y-direction in accordance with an embodiment.

In some embodiments, dynamically removing correlation of parameters of a model of a structure includes a model of a two-dimensional grating structure. The term "two-dimensional grating structure" is used herein to refer to a structure having an x-y profile that varies in only one horizontal dimension in addition to a depth in the z-direction. For example, FIG. 6B depicts a periodic grating 602 having a profile that varies in the x-direction but not in the y-direction, in accordance with an embodiment of the present invention. The profile of the periodic grating varies in the z-direction as a function of the x profile. It is to be understood that the lack of variation in the y-direction for a two-dimensional structure need not be infinite, but any breaks in the pattern are considered long range, e.g., any breaks in the pattern in the y-direction are spaced substantially further apart than the breaks in the pattern in the x-direction.

Embodiments of the present invention may be suitable for a variety of film stacks. For example, in an embodiment, a method for optimizing a parameter of a critical dimension (CD) profile or structure is performed for a film stack including an insulating film, a semiconductor film and a metal film formed on a substrate. In an embodiment, the film stack includes a single layer or multiple layers. Also, in an embodiment invention, an analyzed or measured grating structure includes both a three-dimensional component and a two-dimensional component. For example, the efficiency of a computation based on simulated diffraction data may be optimized by taking advantage of the simpler contribution by the two-dimensional component to the overall structure and the diffraction data thereof.

Figure 7:
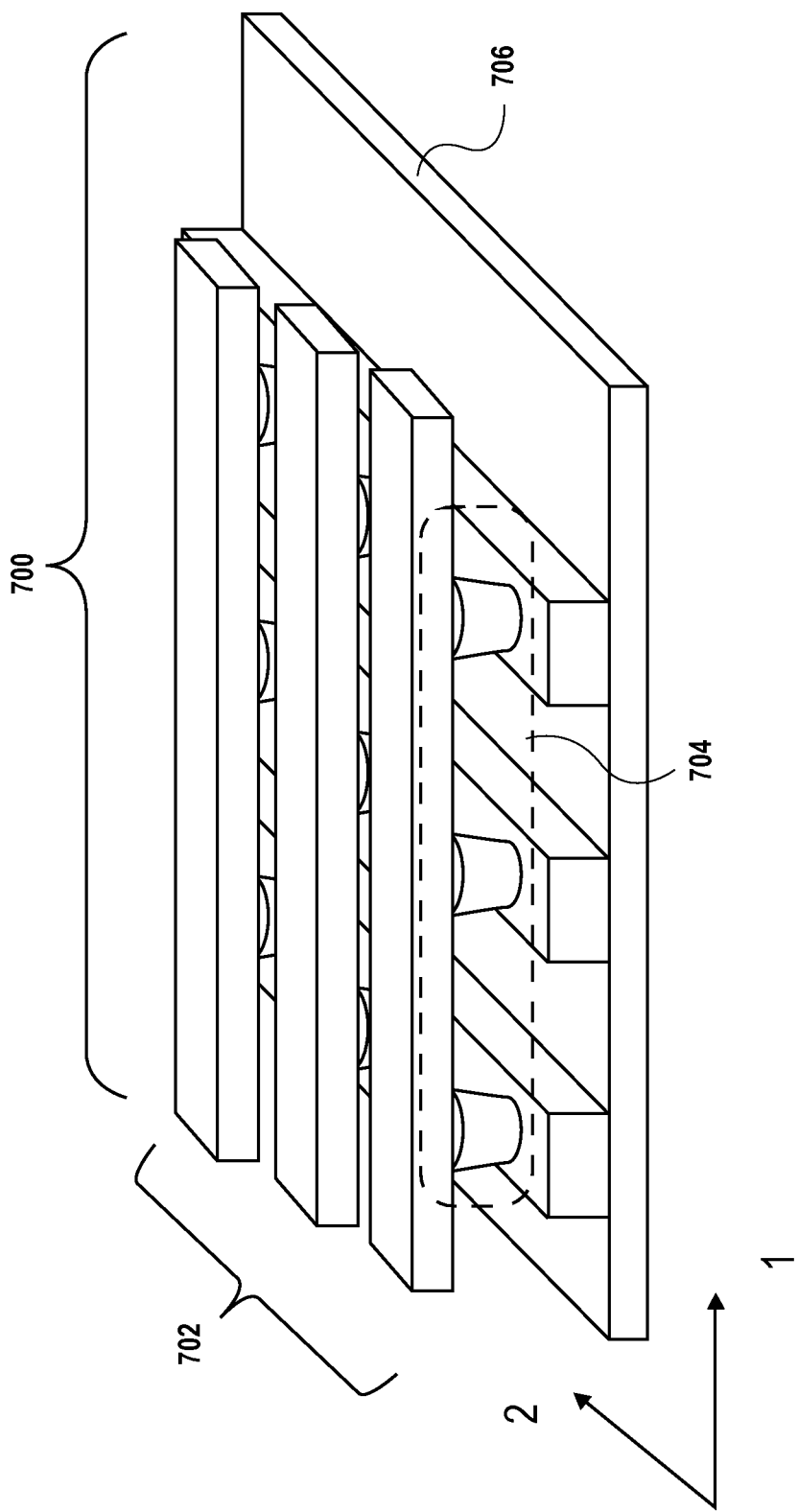
FIG. 7 represents a cross-sectional view of a structure having both a two-dimensional component and a three-dimensional component in accordance with an embodiment.

FIG. 7 represents a cross-sectional view of a structure having both a two-dimensional component and a three-dimensional component, in accordance with an embodiment of the present invention. Referring to FIG. 7, a structure 700 has a two-dimensional component 702 and a three-dimensional component 704 above a substrate 706. The grating of the two-dimensional component runs along direction 2, while the grating of the three-dimensional component runs along both directions 1 and 2. In one embodiment, direction 1 is orthogonal to direction 2, as depicted in FIG. 7. In another embodiment, direction 1 is non-orthogonal to direction 2.

In some embodiments, an apparatus, system, or method provides for dynamic removal of correlation of highly correlated parameters of a model in the measurement of a structure. In some embodiments, the testing may include diffraction signals from a two- or three-dimensional grating structure generated by an ellipsometric optical metrology system, such as the optical metrology systems 800 or 950 described below in association with FIGS. 8 and 9, respectively. However, it is to be understood that the same concepts and principles equally apply to the other optical metrology systems, such as reflectometric systems. The diffraction signals represented may account for features of the two- and three-dimensional grating structure such as, but not limited to, profile, dimension, material composition, or film thickness.

Figure 8:
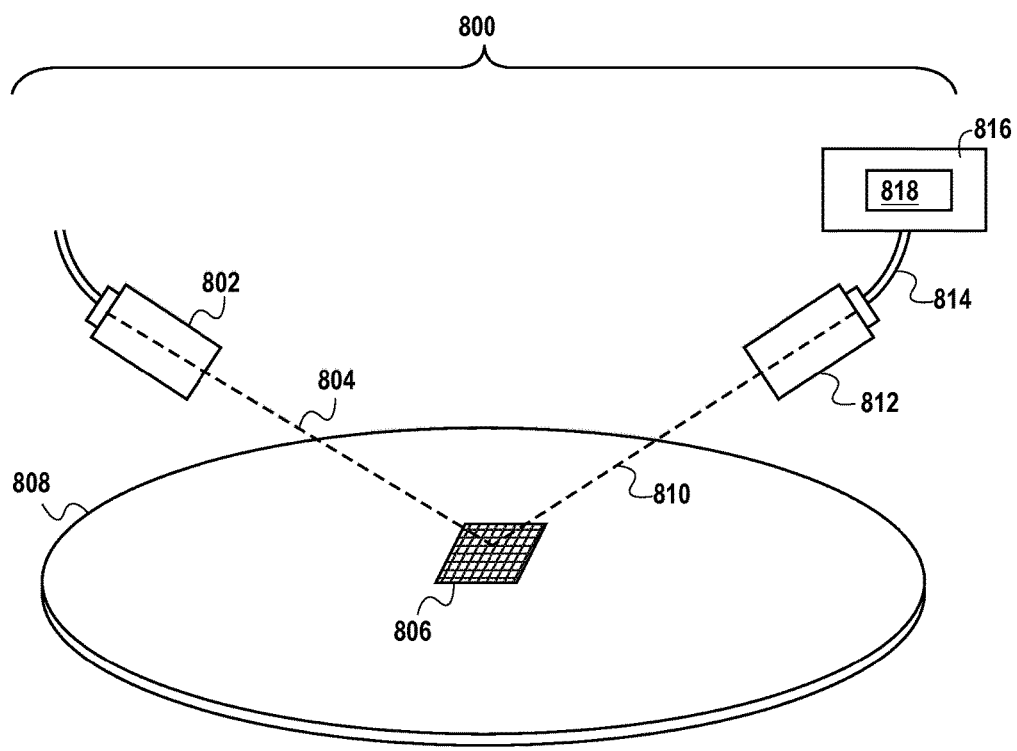
FIG. 8 is a first architectural diagram illustrating the utilization of optical metrology to determine parameters of structures on a semiconductor wafer in accordance with an embodiment.

FIG. 8 is an architectural diagram illustrating the utilization of optical metrology to determine parameters of structures on a semiconductor wafer, in accordance with embodiments of the present invention. The optical metrology system 800 includes a metrology beam source 802 projecting an incident metrology beam 804 at the target structure 806 of a wafer 808. The incident metrology beam 804 is projected at an incidence angle θ towards the target structure 806 (θ is the angle between the incident meteorology beam 804 and a normal to the target structure 806). The ellipsometer may, in one embodiment, use an incidence angle of approximately 60° to 70°, or may use a lower angle (possibly close to 0° or near-normal incidence) or an angle greater than 70° (grazing incidence). The diffraction beam 810 is measured by a metrology beam receiver 812. The diffraction beam data 814 is transmitted to a profile application server 816. The profile application server 816 may compare the measured diffraction beam data 814 against a library 818 of simulated diffraction beam data representing varying combinations of critical dimensions of the target structure and resolution.

In one exemplary embodiment, the library 818 instance best matching the measured diffraction beam data 814 is selected. It is to be understood that although a library of diffraction spectra or signals and associated hypothetical profiles or other parameters is frequently used to illustrate concepts and principles, embodiments of the present invention may apply equally to a data space including simulated diffraction signals and associated sets of profile parameters, such as in regression, neural network, and similar methods used for profile extraction. The hypothetical profile and associated critical dimensions of the selected library 818 instance is assumed to correspond to the actual cross-sectional profile and critical dimensions of the features of the target structure 806. The optical metrology system 800 may utilize a reflectometer, an ellipsometer, or other optical metrology device to measure the diffraction beam or signal.

In order to facilitate the description of embodiments of the present invention, an ellipsometric optical metrology system is used to illustrate the above concepts and principles. It is to be understood that the same concepts and principles apply equally to the other optical metrology systems, such as reflectometric systems. In an embodiment, the optical scatterometry is a technique such as, but not limited to, optical spectroscopic ellipsometry (SE), beam-profile reflectometry (BPR), beam-profile ellipsometry (BPE), and ultra-violet reflectometry (UVR). In a similar manner, a semiconductor wafer may be utilized to illustrate an application of the concept. Again, the methods and processes apply equally to other work pieces that have repeating structures.

Figure 9:
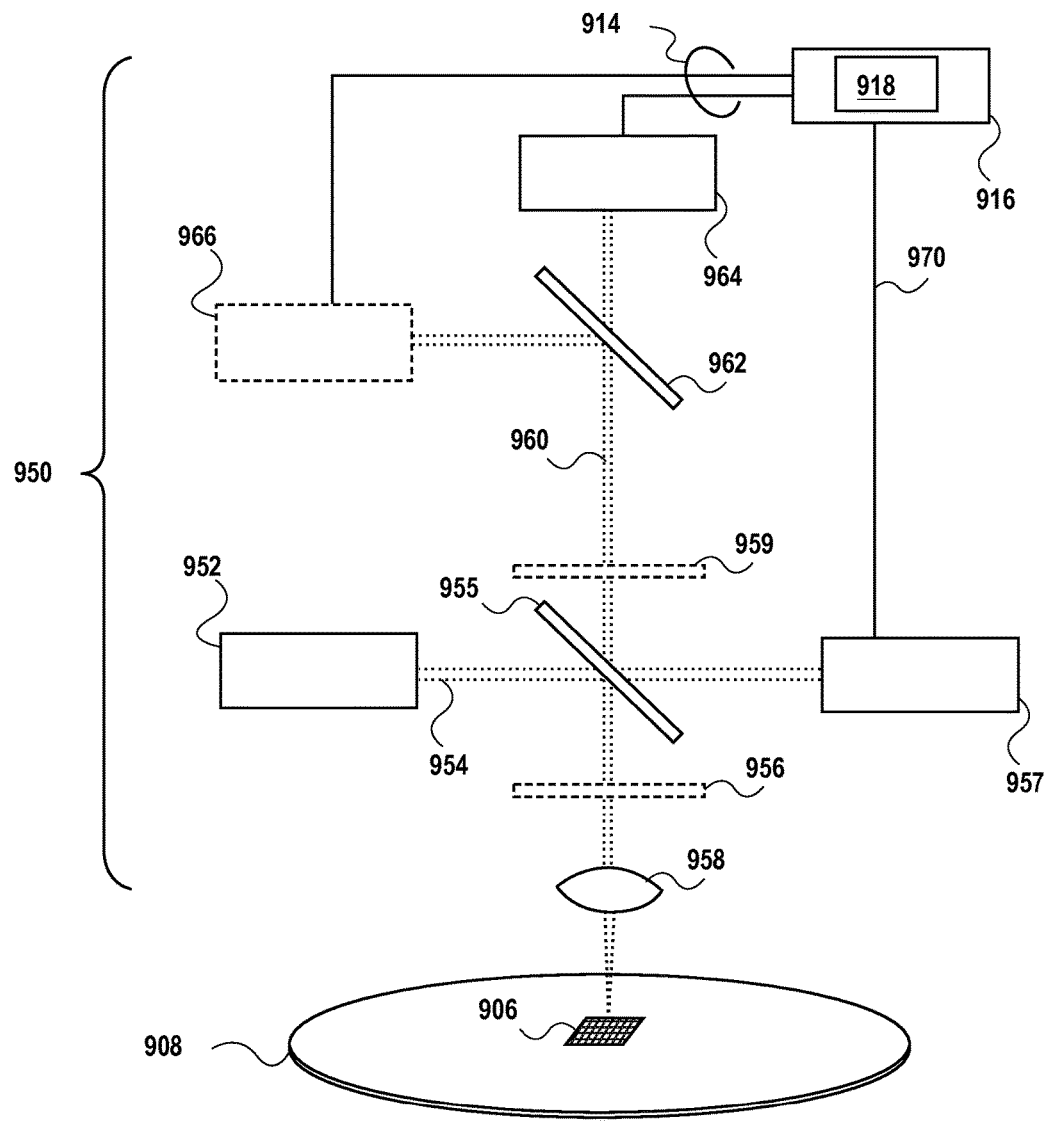
FIG. 9 is a second architectural diagram illustrating the utilization of optical metrology to determine parameters of structures on a semiconductor wafer in accordance with an embodiment.

FIG. 9 is an architectural diagram illustrating the utilization of beam-profile reflectometry, beam-profile ellipsometry, or both to determine parameters of structures on a semiconductor wafer, in accordance with embodiments of the present invention. The optical metrology system 950 includes a metrology beam source 952 generating a polarized metrology beam 954. Preferably this metrology beam has a narrow bandwidth of 10 nanometers or less. In some embodiments, the metrology beam source 952 is capable of outputting beams of different wavelengths by switching filters or by switching between different lasers or superbright light emitting diodes. Part of this beam is reflected from the beam splitter 955 and focused onto the target structure 906 of a wafer 908 by objective lens 958, which has a high numerical aperture (NA), preferably an NA of approximately 0.9 or 0.95. The portion of the polarized metrology beam 954 that is not reflected from the beam splitter is directed to beam intensity monitor 957. The metrology beam may, optionally, pass through a quarter-wave plate 956 before the objective lens 958.

After reflection from the target the reflected beam 960 passes back through the objective lens and is directed to one or more detectors. If optional quarter-wave plate 956 is present, the beam will pass back through that quarter-wave plate before being transmitted through the beam splitter 955. After the beam-splitter, the reflected beam 960 may optionally pass through a quarter-wave plate at location 959 as an alternative to location 956. If the quarter-wave plate is present at location 956, it will modify both the incident and reflected beams. If it is present at location 959, it will modify only the reflected beam. In some embodiments, no wave plate may be present at either location, or the wave plate may be switched in and out depending on the measurement to be made. It is to be understood that in some embodiments it might be desirable that the wave plate have a retardance substantially different from a quarter wave, i.e. the retardance value might be substantially greater than, or substantially less than, 90°.

A polarizer or polarizing beam splitter 962 directs one polarization state of the reflected beam 960 to detector 964, and, optionally, directs a different polarization state to an optional second detector 966. The detectors 964 and 966 might be one-dimensional (line) or two-dimensional (array) detectors. Each element of a detector corresponds to a different combination of AOI and azimuthal angles for the corresponding ray reflected from the target. The diffraction beam data 914 from the detector(s) is transmitted to the profile application server 916 along with beam intensity data 970. The profile application server 916 may compare the measured diffraction beam data 914 after normalization or correction by the beam intensity data 970 against a library 918 of simulated diffraction beam data representing varying combinations of critical dimensions of the target structure and resolution.

For more detailed descriptions of systems that could be used to measure the diffraction beam data or signals for use with the present invention, see U.S. Pat. No. 6,734,967, entitled FOCUSED BEAM SPECTROSCOPIC ELLIPSOMETRY METHOD AND SYSTEM, filed on Feb. 11, 1999, and U.S. Pat. No. 6,278,519 entitled APPARATUS FOR ANALYZING MULTI-LAYER THIN FILM STACKS ON SEMICONDUCTORS, filed Jan. 29, 1998, both of which are incorporated herein by reference in their entirety. These two patents describe metrology systems that may be configured with multiple measurement subsystems, including one or more of a spectroscopic ellipsometer, a single-wavelength ellipsometer, a broadband reflectometer, a DUV reflectometer, a beam-profile reflectometer, and a beam-profile ellipsometer. These measurement subsystems may be used individually, or in combination, to measure the reflected or diffracted beam from films and patterned structures. The signals collected in these measurements may be analyzed to determine parameters of structures on a semiconductor wafer in accordance with embodiments of the present invention.

Embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 10:
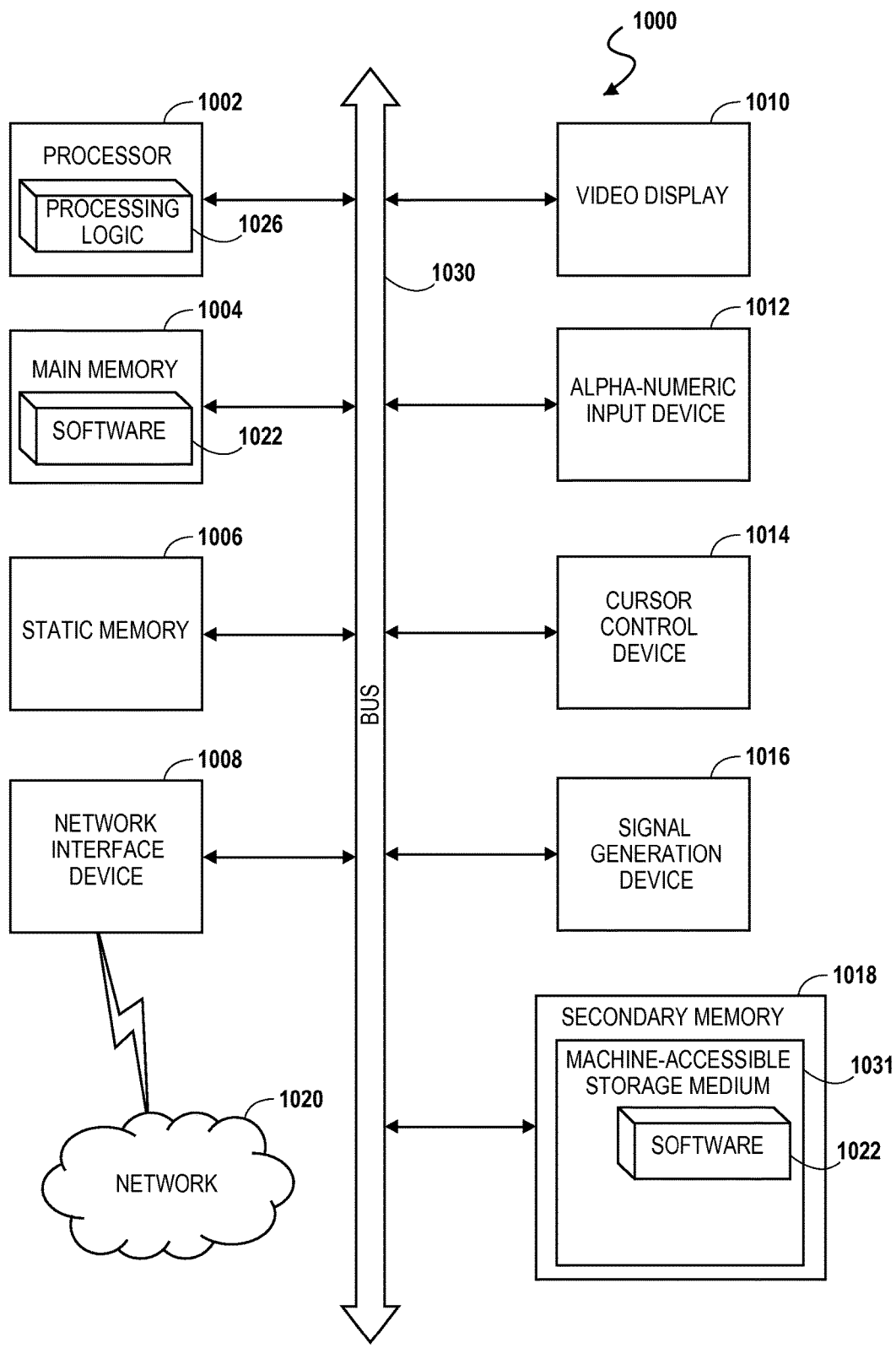
FIG. 10 illustrates a block diagram of an exemplary computer system in accordance with an embodiment.

FIG. 10 illustrates a diagrammatic representation of a machine in the exemplary form of a computer system 1000 within which a set of instructions, for causing the machine to perform any one or more of the methodologies discussed herein, may be executed, according to embodiments. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1000 includes a processor 1002, a main memory 1004 (e.g., read-only memory (ROM), flash memory, dynamic random access memory (DRAM) such as synchronous DRAM (SDRAM) or Rambus DRAM (RDRAM), etc.), a static memory 1006 (e.g., flash memory, static random access memory (SRAM), etc.), and a secondary memory 1018 (e.g., a data storage device), which communicate with each other via a bus 1030.

Processor 1002 represents one or more general-purpose processing devices such as a microprocessor, central processing unit, or the like. More particularly, the processor 1002 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1002 may also be one or more special-purpose processing devices such as an application specific integrated circuit (ASIC), a field programmable gate array (FPGA), a digital signal processor (DSP), network processor, or the like. Processor 1002 is configured to execute the processing logic 1026 for performing the operations discussed herein.

The computer system 1000 may further include a network interface device 1008. The computer system 1000 also may include a video display unit 1010 (e.g., a liquid crystal display (LCD) or a cathode ray tube (CRT)), an alphanumeric input device 1012 (e.g., a keyboard), a cursor control device 1014 (e.g., a mouse), and a signal generation device 1016 (e.g., a speaker).

The secondary memory 1018 may include a machine-accessible storage medium (or more specifically a computer-readable storage medium) 1031 on which is stored one or more sets of instructions (e.g., software 1022) embodying any one or more of the methodologies or functions described herein. The software 1022 may also reside, completely or at least partially, within the main memory 1004 and/or within the processor 1002 during execution thereof by the computer system 1000, the main memory 1004 and the processor 1002 also constituting machine-readable storage media. The software 1022 may further be transmitted or received over a network 1020 via the network interface device 1008.

While the machine-accessible storage medium 1031 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

In accordance with an embodiment of the present invention, a machine-accessible storage medium has instructions stored thereon that cause a data processing system to perform a method of dynamic removal of correlation of highly-correlated parameters of a structure.

It is to be understood that the above methodologies may be applied under a variety of circumstances within the spirit and scope of embodiments of the present invention. For example, in an embodiment, measurements described above are performed with or without the presence of background light. In an embodiment, a method described above is performed in a semiconductor, solar, light-emitting diode (LED), or a related fabrication process. In an embodiment, a method described above is used in a stand-alone or an integrated metrology tool.

Figure 11:
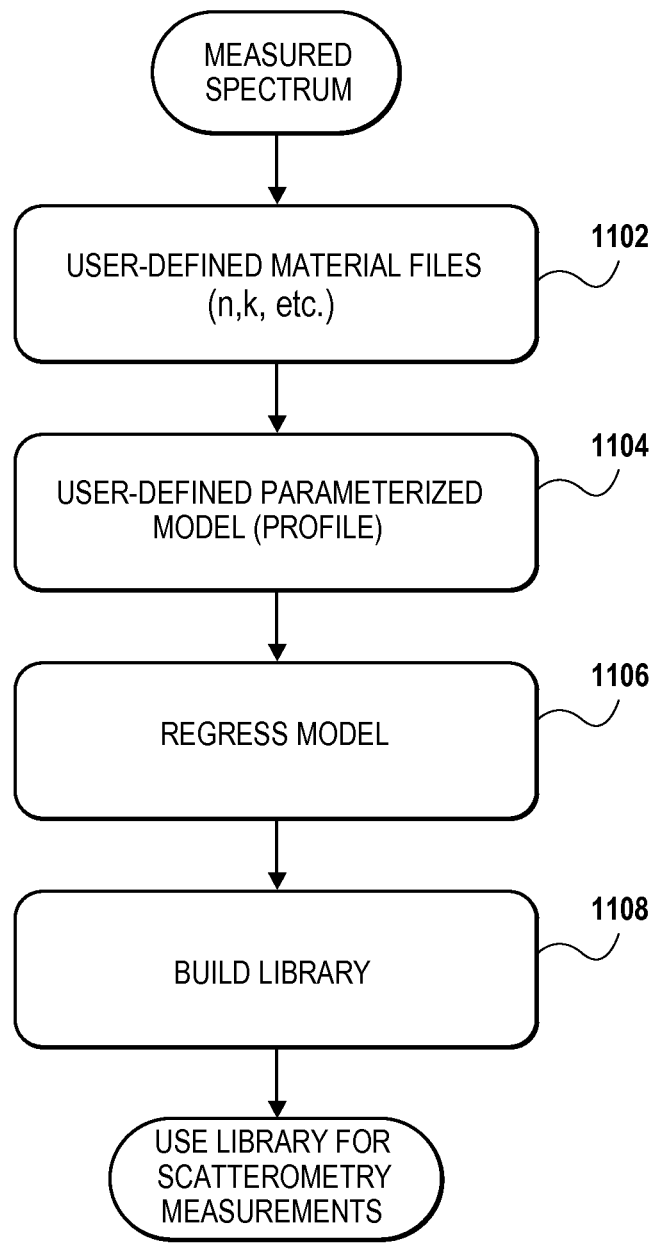
FIG. 11 is a flowchart representing operations in a method for a building parameterized model and a spectral library beginning with sample spectra in accordance with an embodiment.

Analysis of measured spectra generally involves comparing the measured sample spectra to simulated spectra to deduce parameter values of a model that best describe the measured sample. FIG. 11 is a flowchart 1100 representing operations in a method for a building parameterized model and a spectral library beginning with sample spectra (e.g., originating from one or more work pieces), in accordance with an embodiment of the present invention.

At operation 1102, a set of material files are defined by a user to specify characteristics (e.g., refractive index or n, k values) of the material(s) from which the measured sample feature is formed.

At operation 1104, a scatterometry user defines a nominal model of the expected sample structure by selecting one or more of the material files to assemble a stack of materials corresponding to those present in the periodic grating features to be measured. Such a user-defined model may be further parameterized through definition of nominal values of model parameters, such as thicknesses, critical dimension (CD), sidewall angle (SWA), height (HT), edge roughness, corner rounding radius, etc. which characterize the shape of the feature being measured. Depending on whether a two-dimensional model (i.e., a profile) or three-dimensional model is defined, it is not uncommon to have 30-50, or more, such model parameters.

From a parameterized model, simulated spectra for a given set of grating parameter values may be computed using rigorous diffraction modeling algorithms, such as rigorous coupled wave analysis (RCWA). Regression analysis is then performed at operation 1106 until the parameterized model converges on a set of parameter values characterizing a final profile model (for two-dimensional) that corresponds to a simulated spectrum which matches the measured diffraction spectra to a predefined matching criterion. The final profile model associated with the matching simulated diffraction signal is presumed to represent the actual profile of the structure from which the model was generated.

The matching simulated spectra and/or associated optimized profile model can then be utilized at operation 1108 to build a library of simulated diffraction spectra by perturbing the values of the parameterized final profile model. The resulting library of simulated diffraction spectra may then be employed by a scatterometry measurement system operating in a production environment to determine whether subsequently measured grating structures have been fabricated according to specifications. Library generation 1108 may include a machine learning system, such as a neural network, generating simulated spectral information for each of a number of profiles, each profile including a set of one or more modeled profile parameters. In order to generate the library, the machine learning system itself may have to undergo some training based on a training data set of spectral information. Such training may be computationally intensive and/or may have to be repeated for different models and/or profile parameter domains. Considerable inefficiency in the computational load of generating a library may be introduced by a user's decisions regarding the size of a training data set. For example, selection of an overly large training data set may result in unnecessary computations for training while training with a training data set of insufficient size may necessitate a retraining to generate a library.

For some applications it may be unnecessary to build a library. After the parametric model of the structure has been created and optimized, a regression analysis similar to that described above may be used in real time to determine the best fitting parameter values for each target as the diffraction beam data are collected. If the structure is relatively simple (for example a 2D structure), or if only a small number of parameters need to be measured, regression may be fast enough even though it may be slower than using a library. In other cases, the extra flexibility of using regression may justify some increase in measurement time over using a library. For a more detailed description of methods and systems that are capable of real-time regression of OCD data for use with the present invention, see U.S. Pat. No. 7,031,848, entitled REAL TIME ANALYSIS OF PERIODIC STRUCTURES ON SEMICONDUCTORS, filed on Jul. 8, 2005, which is incorporated herein by reference in its entirety.

In the description above, for the purposes of explanation, numerous specific details are set forth in order to provide a thorough understanding of the described embodiments. It will be apparent, however, to one skilled in the art that embodiments may be practiced without some of these specific details. In other instances, well-known structures and devices are shown in block diagram form. There may be intermediate structure between illustrated components. The components described or illustrated herein may have additional inputs or outputs that are not illustrated or described.

Various embodiments may include various processes. These processes may be performed by hardware components or may be embodied in computer program or machine-executable instructions, which may be used to cause a general-purpose or special-purpose processor or logic circuits programmed with the instructions to perform the processes. Alternatively, the processes may be performed by a combination of hardware and software.

Portions of various embodiments may be provided as a computer program product, which may include a computer-readable medium having stored thereon computer program instructions, which may be used to program a computer (or other electronic devices) for execution by one or more processors to perform a process according to certain embodiments. The computer-readable medium may include, but is not limited to, magnetic disks, optical disks, compact disk read-only memory (CD-ROM), and magneto-optical disks, read-only memory (ROM), random access memory (RAM), erasable programmable read-only memory (EPROM), electrically-erasable programmable read-only memory (EEPROM), magnet or optical cards, flash memory, or other type of computer-readable medium suitable for storing electronic instructions. Moreover, embodiments may also be downloaded as a computer program product, wherein the program may be transferred from a remote computer to a requesting computer.

Many of the methods are described in their most basic form, but processes can be added to or deleted from any of the methods and information can be added or subtracted from any of the described messages without departing from the basic scope of the present embodiments. It will be apparent to those skilled in the art that many further modifications and adaptations can be made. The particular embodiments are not provided to limit the concept but to illustrate it. The scope of the embodiments is not to be determined by the specific examples provided above but only by the claims below.

If it is said that an element "A" is coupled to or with element "B," element A may be directly coupled to element B or be indirectly coupled through, for example, element C. When the specification or claims state that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification or claim refers to "a" or "an" element, this does not mean there is only one of the described elements.

An embodiment is an implementation or example. Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. It should be appreciated that in the foregoing description of exemplary embodiments, various features are sometimes grouped together in a single embodiment, figure, or description thereof for the purpose of streamlining the disclosure and aiding in the understanding of one or more of the various novel aspects. This method of disclosure, however, is not to be interpreted as reflecting an intention that the claimed embodiments requires more features than are expressly recited in each claim. Rather, as the following claims reflect, novel aspects lie in less than all features of a single foregoing disclosed embodiment. Thus, the claims are hereby expressly incorporated into this description, with each claim standing on its own as a separate embodiment.

What is claimed is:

1. A method for optical metrology testing of a microelectronic structure comprising:
    determining a model of a first microelectronic structure on a substrate using a processor, the model of the first microelectronic structure including a set of model parameters, the set of model parameters including geometric parameters, material parameters, or both;
    performing optical metrology measurement of the first microelectronic structure utilizing an optical metrology system to determine a value of at least one parameter of the first microelectronic structure, including collecting measured spectra data for the first microelectronic structure on a hardware element, the hardware element being a reflectometer or ellipsometer;
    during the optical metrology measurement of the first microelectronic structure, dynamically removing correlation of two or more parameters of the set of model parameters using the processor, wherein the dynamic removal of correlation of parameters during the optical metrology measurement does not change the model of the microelectronic structure, each iteration of the dynamic removal of correlation during the optical metrology measurement including:
        generating a Jacobian matrix of the set of model parameters, wherein generating the matrix includes inputting the measured spectra data for the microelectronic structure collected by the hardware element, applying a singular value decomposition of the Jacobian matrix, wherein the application of the singular value decomposition results in a set of singular vectors, selecting a subset of the set of singular vectors, wherein selecting the subset of vectors includes applying a threshold, the threshold being adaptively selected based on the number of iterations of the dynamic removal of correlation that are performed, and computing a direction of the parameter search based on the subset of vectors;

if the model of the first microelectronic structure does not converge following an iteration of the dynamic removal of correlation, performing one or more additional iterations of the dynamic removal of correlation until the model converges;

if the model of the first microelectronic structure does converge, reporting out results of the optical metrology measurement of the first microelectronic structure including the value of the at least one parameter of the first microelectronic structure based on comparison of the measured spectra data for the first microelectronic structure with a simulated diffraction signal for the model of the first microelectronic structure; and modifying a process variable or an equipment setting of a fabrication cluster using the results that include the value of the at least one parameter, wherein the fabrication cluster is configured to perform semiconductor manufacturing.

2. The method of claim 1, further comprising applying one or more constraints on parameters of the model of the first microelectronic structure to remove mathematical uncertainty in the dynamic removal of correlation of parameters, wherein the one or more constraints are constraints based on knowledge regarding geometry of the model or values of parameters of the model.

3. The method of claim 2, wherein applying the one or more constraints includes applying the one or more constraints once upon convergence of the model.

4. The method of claim 2, wherein applying the one or more constraints includes applying the one or more constraints in each iteration of the dynamic removal of correlation.

5. The method of claim 1, further comprising storing the model parameters and the optical metrology measurements in a computer memory.

6. The method of claim 1, wherein the threshold is a relative threshold, the contribution of the subset of vectors being required to be equal to or greater than the threshold.

7. The method of claim 1, wherein the threshold is an absolute value, each chosen vector being required to be greater than the threshold value.

8. The method of claim 7, wherein the threshold is linked with a noise specification for the hardware element on which the spectra data is collected.

9. The method of claim 1, wherein the value of the threshold is modified based on the number of iterations of the dynamic removal of correlation that are performed.

10. The method of claim 1, wherein the ellipsometer or reflectometer is one of a spectroscopic or angle-resolved ellipsometer or spectroscopic or angle-resolved reflectometer.

11. A non-transitory, tangible machine-accessible storage medium having instructions stored thereon that cause a data processing system to perform a method of dynamic removal of correlation of parameters, the method comprising:

determining a model of a first microelectronic structure on a substrate, the model of the first microelectronic structure including a set of model parameters, the set of model parameters including geometric parameters, material parameters, or both;

performing optical metrology measurement of the first microelectronic structure utilizing an optical metrology system to determine a value of at least one parameter for the first microelectronic structure, including collecting measured spectra data for the first microelectronic structure on a hardware element, the hardware element being a reflectometer or ellipsometer;

during the optical metrology measurement of the first microelectronic structure, dynamically removing correlation of two or more parameters of the set of model parameters, wherein the dynamic removal of correlation of parameters during the optical metrology measurement does not change the model of the microelectronic structure, each iteration of the dynamic removal of correlation during the optical metrology measurement including:

generating a Jacobian matrix of the set of model parameters, wherein generating the matrix includes inputting the measured spectra data for the microelectronic structure collected by the hardware element, applying a singular value decomposition of the Jacobian matrix, wherein the application of the singular value decomposition results in a set of singular vectors, selecting a subset of the set of vectors, wherein selecting the subset of vectors includes applying a threshold, the threshold being adaptively selected based on the number of iterations of the dynamic removal of correlation that are performed, and computing a direction of the parameter search based on the subset of vectors;

if the model of the first microelectronic structure does not converge following an iteration of the dynamic removal of correlation, performing one or more additional iterations of the dynamic removal of correlation until the model converges;

if the model of the microelectronic structure does converge, reporting results of the optical metrology measurement of the first microelectronic structure including the value of the at least one parameter of the first microelectronic structure based on comparison of the measured spectra data for the first microelectronic structure with a simulated diffraction signal for the model of the first microelectronic structure; and modifying a process variable or an equipment setting of a fabrication cluster using the results that include the value of the at least one parameter, wherein the fabrication cluster is configured to perform semiconductor manufacturing.

12. The storage medium of claim 11, wherein the method further comprises:

applying one or more constraints on parameters of the model of the first microelectronic structure to remove mathematical uncertainty in the dynamic removal of correlation of parameters, wherein the one or more constraints are constraints based on knowledge regarding the geometry of the model or values of parameters of the model.

13. The storage medium of claim 12, wherein applying the one or more constraints includes applying the one or more constraints once upon convergence of the model.

14. The storage medium of claim 12, wherein applying the one or more constraints includes applying the one or more constraints in each iteration of the dynamic removal of correlation.

15. The storage medium of claim 11, wherein the method further comprises:
storing the model parameters and the optical metrology measurements in a computer memory.

16. The storage medium of claim 11, wherein the threshold is a relative threshold, the contribution of the subset of vectors being required to be equal to or greater than the threshold.

17. The storage medium of claim 11, wherein the threshold is an absolute value, each chosen vector being required to be greater than the threshold value.

18. The storage medium of claim 17, wherein the threshold is linked with a noise specification for the hardware element on which the spectra data is collected.

19. The storage medium of claim 11, wherein the value of the threshold is modified based on the number of iterations of the dynamic removal of correlation.

20. The storage medium of claim 11, wherein the ellipsometer or reflectometer is one of a spectroscopic or angle-resolved ellipsometer or spectroscopic or angle-resolved reflectometer.

21. A system for optical metrology testing of a microelectronic structure comprising:
an optical metrology system including a reflectometer or ellipsometer, the optical metrology system configured to determine a value of at least one parameter of a first microelectronic structure on a substrate, the optical metrology system comprising:
a beam source that projects a beam at the substrate and detector configured to measure a diffraction signal of the microelectronic structure by receiving the beam reflected from the substrate; and
a processor configured to determine a model of the first microelectronic structure and process measurement data for the first microelectronic structure from the detector, the model including a set of model parameters, the set of model parameters including geometric parameters, material parameters, or both;
wherein the optical metrology system is configured to:
perform optical metrology measurement of the microelectronic structure, including collecting measured spectra data for the microelectronic structure,
during the optical metrology measurement of the first microelectronic structure, dynamically remove correlation of two or more parameters of the set of model parameters, wherein the dynamic removal of correlation of parameters during the optical metrology measurement does not change the model of the microelectronic structure, each iteration of the dynamic removal of correlation during the optical metrology measurement including:
generating a Jacobian matrix of the set of model parameters, wherein generating the matrix includes inputting the measured spectra data for the microelectronic structure collected by the hardware element,
applying a singular value decomposition of the Jacobian matrix, wherein the application of the singular value decomposition results in a set of singular vectors,
selecting a subset of the set of singular vectors, wherein selecting the subset of vectors includes applying a threshold, the threshold being adaptively selected based on the number of iterations of the dynamic removal of correlation that are performed, and
computing a direction of the parameter search based on the subset of vectors;
if the model of the first microelectronic structure does not converge following an iteration of the dynamic removal of correlation, perform one or more additional iterations of the dynamic removal of correlation until the model converges;
if the model of the first microelectronic structure does converge, report results of the optical metrology measurement of the first microelectronic structure including the value of the at least one parameter of the first microelectronic structure based on comparison of the measured spectra data for the first microelectronic structure with a simulated diffraction signal for the model of the first microelectronic structure; and
modify a process variable or an equipment setting of a fabrication cluster using the results that include the value of the at least one parameter, wherein the fabrication cluster is configured to perform semiconductor manufacturing.

22. The system of claim 21, wherein the ellipsometer or reflectometer is one of a spectroscopic or angle-resolved ellipsometer or spectroscopic or angle-resolved reflectometer.

* * * * *